United States Patent [19]

Diethelm

[11] 4,292,318
[45] Sep. 29, 1981

[54] PRODUCT AND METHOD FOR COMBATING SWINE DYSENTERY

[75] Inventor: Eugen Diethelm, Triesen, Liechtenstein

[73] Assignee: Grissman Chemicals Limited, England

[21] Appl. No.: 157,100

[22] Filed: Jun. 6, 1980

[30] Foreign Application Priority Data

Jul. 10, 1979 [GB] United Kingdom ............... 24003/79

[51] Int. Cl.³ .......................................... A61K 31/495
[52] U.S. Cl. ................................................ 424/250
[58] Field of Search ......................................... 424/250

[56] References Cited

U.S. PATENT DOCUMENTS 3,720,768  3/1973  Jones ................................... 424/250

OTHER PUBLICATIONS

Bacikova et al., Chem. Abst., vol. 63 (1965), p. 12044e.
Coutts et al., Chem. Abst., vol. 63 (1965), p. 5598b.

*Primary Examiner*—Sam Rosen

*Attorney, Agent, or Firm*—Ostrolenk, Faber, Gerb & Soffen

[57] ABSTRACT

A substituted pyrazine having the formula

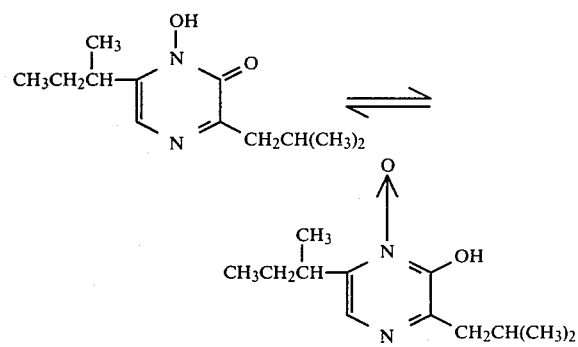

is useful for treating and preventing swine dysentery. It may be administered to swine in an effective but non-toxic amount in the form of the drug per se, or a feed composition. Such feeds may be made with the aid of premixes containing the said compound.

5 Claims, No Drawings

PRODUCT AND METHOD FOR COMBATING SWINE DYSENTERY

DESCRIPTION

This invention relates to the treatment and prevention of swine dysentery, and to products for use therein.

Swine dysentery (also known as vibrionic dysentery, bloody scours, or hemorrhagic dysentery) is an enteric disease primarily characterised by muco-hemorrhagig diarrhea with lesions usually restricted to the large intestine. The disease is worldwide and is a major disease problem among swine producers all over the world.

The earlier consensus was the *Vibrio coli* was the primary causative agent. Recent evidence suggests, however, that a spirochete, *Treponema hyodysenteriae* is involved with the disease and may in fact be the primary etiologic agent.

Currently, control measures are based on constant feeding of antibacterial agents with therapy based on use of high levels of these drugs. The drugs used include furazolidone, neomycin, oxytetracycline, tylosin, carbadox, virginiamycin and arsanilic acid. Unfortunately, these drugs give erratic results, even when used at abnormally high levels.

Accordingly there is a continuing need for new drugs of low toxicity and high potency to combat swine dysentery.

It has now been discovered that a substituted pyrazine of that formula:

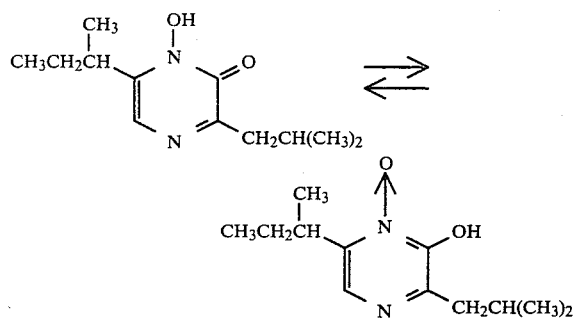

hereinafter referred to as "D-compound" is useful in veterinary therapy for the treatment and prophylaxis of swine dysentery. This compound selectively combats the swine dysentery-causing organisms without deleteriously affecting the balance of other desired organisms, e.g. in the internal biological system of swine, such as the intestinal flora.

The antibiotic substance D-aspergillic acid which has been isolated from cultures of *Aspergillus flavus* conform to the aforesaid formula.

In the method of the present invention, the D-Compound is administered to swine in an amount effective to combat dysentery. It can be advantageously incorporated in a swine feed-stock to provide a swine feed composition for combatting dysentery. It can be incorporated in the swine feed-stock generally at a level of from about 25 g/ton to about 500 g/ton. The preferred level, however, particularly in the absence of the disease, is about 100 to 200 g/ton for prophylaxis, advantageously for a period of 3 to 21 days. However, it there has been an outbreak of the disease, or if new animals whose history is not known have been introduced into a herd, the higher level of 200 to 500 g/ton is preferred until the health of the herd is assured. Generally, however, the prophylactic treatment is continued until the animals are ready for market. The D-Compound can also be administered by incorporation into drinking water provided for swine.

The D-Compound is useful for combatting swine dysentery-causing organisms, e.g. dysentery caused by Vibrio or Treponema organisms, or both. The D-Compound is of a low order of toxicity and is suitable for use by oral administration for prophylactic or therapeutic treatment of swine dysentery. It is not nitrogenic.

A swine feed-stock for oral administration of D-Compound according to this invention can be readily prepared by intimately admixing the D-Compound alone or as a premix with a conventional swine feed composition to provide a homogeneous feed product.

The term feed-stock means any food provided for the swine. Preferably the D-Compound is thoroughly mixed with the feed-stock so that it is uniformly dispersed throughout. However, it may also be sprinkled on the daily food supplies in the form of a powder or as pellets. Thus, the invention is not limited to any particular mode of administration.

The following Example illustrates the invention.

EXAMPLE

The D-Compound was tested against five strains of *Vibrio cholerae* at concentrations of 10, 30 and 100 micrograms per milliliter. The results are given in Table 1 below.

Tests were also run to see if the compound was effective against *Vibrio cholerae* El Tor Ogawa 6 in the presence of sewage. Sewage samples were obtained from the sewer system of the city of Modena, Italy. They were centrifuged to separate solids and the supernatant liquid was used in the tests. The results are given in Table 2.

At 10 mcg/ml of D, there was no growth of 3 of the organisms after 48 hours, and only marginal growth of the remaining two at 100 mcg/ml.

D was tested in vitro against *Treponema hyodysenteriae* by a known method. The minimum inhibitory concentration (the lowest concentration of compound in a dilution series where growth is inhibited) was 0.1 mcg/ml. The minimum bactericidal concentration (the lowest concentration of compound in which no viable treponemes are observed upon dilution and subculture from the broth onto blood agar plates) was greater than 0.1 mcg/ml but less than 1 mcg/ml.

The compound was tested for acute toxicity by several modes of administration in four species, namely mice, rat, guinea pig, and rabbit. The compound was found to be of a low order of toxicity. The results are given below in Tables 3, 4, 5 and 6.

In view of the favourable acute toxicity data, the compound was administered orally in sub-acute, but relatively large, doses to mice and rats for 15 days. Data were collected on the effects on death rate, weight, liver, and kidneys. The data are given in Tables 7 and 8.

In view of the favourable results on chronic toxicity, a teratogenic study was conducted with male and female mice and rats. The number of young delivered live at birth was comparable with controls. No malformations in either group were observed. The data are given in Table 10.

TABLE 1

| Compound | Concentration μg/ml | Effect on Various Strains of *Vibrio Cholerae* | | | | |
|---|---|---|---|---|---|---|
| | | Classical Inaba 35 | Classical Ogawa 41 | El Tor Ogawa 6 | El Tor Ogawa 8 | El Tor Inaba 4 |
| D | 100 | — | — | ± | — | ± |
| | 30 | — | — | — | — | ++ |
| | 10 | — | — | ++ | — | ++ |

— No growth after 48 hours at 37° C.
± Just noticeable growth
+ Evident growth but to a smaller extent than in untreated control experiments
++ Same degree of growth as in untreated control experiments.

TABLE 2

| Sample | Concentration of D | Effect After | | |
|---|---|---|---|---|
| | | 24 hours | 48 hours | 5 days |
| Control + Vibrion | — | +++ | +++ | +++ |
| Sewage | — | --- | --- | --- |
| Sewage + Vibrion | — | +++ | +++ | +++ |
| Sewage + Vibrion | 5γ/ml | --- | --- | --- |
| Sewage + Vibrion | 10γ/ml | --- | --- | --- |
| Sewage + Vibrion | 20γ/ml | --- | --- | --- |
| Sewage + Vibrion | 30γ/ml | --- | --- | --- |

TABLE 3

Acute Toxicity of D in female Mice

| Dosage mg/kg | Dead/Treated Animals after | | | |
|---|---|---|---|---|
| | 1 day | 2 days | 4 days | 7 days |
| | Endoperitoneal Administration | | | |
| 2000 | 6/6 | | | 6/6 |
| 1000 | | 6/6 | | 6/6 |
| 500 | | | | 6/12 |
| 250 | | | | 0/18 |
| | Esophageal Administration | | | |
| 0 (x) | | | | 0/6 |
| 4000 | | | 1/12 | 1/12 |
| 2000 | | | | 0/12 |
| 1000 | | | | 0/12 |

(x) By gastric lavage and receiving only the vehicle.

TABLE 4

Acute Toxicity of D in the Rat a. First Experiment

| Sex | Route of Administration | mg/kg | Dead/Treated within 21 days | Body weight in g. start | (m ± SEM) Termination | Statistical Significance(·) |
|---|---|---|---|---|---|---|
| M | Esophageal | 4000 | 0/4 | 234.5 ± 13.8 | 288.7 ± 13.8 | t 0.05 |
| M | Esophageal | 0 (x) | ¼ | 233.7 ± 3.7 | 331.0 ± 0.5 | |
| F | Esophageal | 4000 | 0/4 | 201.2 ± 4.2 | 238.2 ± 12.1 | t 0.05 |
| F | Esophageal | 0 (x) | ¼ | 189.2 ± 3.9 | 230.0 ± 10.5 | |
| M | Endoperitoneal | 500 | ¼ | 234.0 ± 6.2 | 314.3 ± 10.3 | t 0.05 |
| M | Endoperitoneal | 0 (x) | 0/4 | 230.0 ± 5.7 | 324.0 ± 8.7 | |
| F | Endoperitoneal | 500 | 2/4 | 206.2 ± 8.7 | 286.0 − 272.0 | t 0.05 |
| F | Endoperitoneal | 0 (x) | 0/4 | 207.5 ± 4.3 | 253.5 ± 7.7 | |

(x) Only the vehicle was administered by the same route.
(·) Student's t test.

b. Second Experiment

| Sex | Route of Administration | mg/kg | Dead/Treated within 7 days | Body weight in g. start | (±SE) Termination |
|---|---|---|---|---|---|
| M | Esophageal | 4000 | 0/4 | 222.5 ± 6.2 | 231.7 ± 15.7 |
| F | Esophageal | 4000 | 0/4 | 252.0 ± 16.6 | 253.5 ± 12.1 |
| M | Intraperitoneal | 500 | 2/4 | 226.2 ± 6.8 | 225.0 − 212 |
| F | Intraperitoneal | 500 | 0/4 | 232.5 ± 5.9 | 218.2 ± 7.0 | c. Cumulative Data Regardless of Animal Sex

| Route of Administration | mg/kg | Dead/Treated within 7 days |
|---|---|---|
| Esophageal | 0 (x) | 0/8 |
| Esophageal | 4000 | 0/16 |
| Intraperitoneal | 0 (x) | 0/8 |
| Intraperitoneal | 500 | 4/16 |

(x) Only the vehicle was administered.

TABLE 5

Acute Toxicity of D in the Guinea Pig By Esophageal Administration

| Dosage mg/kg | Dead/Treated within 21 days |
|---|---|
| 500 | 0/4 |
| 1000 | 1/4 |
| 2000 | 5/6 |
| 4000 | 6/6 |
| 0(x) | 0/13 |

(x) Only the vehicle was administered.

TABLE 6

Acute Toxicity of D in the Rabbit By Esophageal Administration

| Dosage mg/kg | Dead/Treated within 7 days | Body Weight in g. start | (m ± SE) Termination |
|---|---|---|---|
| 2000 | 0/2(·) | 2250 − 2150 | 2180 − 2140 |
| 1000 | 0/4 | 2037 ± 104.3 | 1922.5 ± 71.5 |
| 0(x) | 0/4 | 2135 ± 75 | 2262 ± 215 |
| 500 | 0/2 | 2000 − 2100 | 1650 − 1550 |

(x) Only the vehicle was administered.
(·) There were two dead out of seven treated animals, within 4 days.

TABLE 7

Subacute Toxicity of D in the Mouse
Daily Dose: 500 mg. CO-1 by gastric lavage for 15 days

| Oral Treatment | Dead/ Treated | % Body Weight Change (m + SE) | Fresh Organ-to-Body Weight Ratio | |
|---|---|---|---|---|
| | | | Liver | Kidneys |
| Vehicle | 0/10 | 20.4 ± 4.2 | 5.2 ± 0.2 | 1.4 ± 0.1 |
| CO-1, 500 mg/kg/day | 0/10 | −8.1 ± 3.9 | 5.9 ± 0.3 | 1.5 ± 0.1 | a. Mortality and Body Weight
Daily Dose: 1 g/kg/day for 15 days

| Oral Treatment | Dead/ Treated | % Body Weight Change |
|---|---|---|

TABLE 7-continued

Subacute Toxicity of D in the Mouse
Daily Dose: 500 mg. CO-1 by gastric lavage for 15 days

| | | |
|---|---|---|
| Vehicle (H₂O) | 0/12 | 24.54 ± 0.64 |
| CO-1 in H₂O, 1 g/kg/day | 2/12 | 18.5 ± 0.75 |
| Vehicle (adraganth gum) (x) | 0/12 | 25.04 ± 1.18 |
| CO-1 in adraganth gum | 3/12 | 16.27 ± 1.31 | b. SGOT and SGPT (24 hrs. after last dose)

| Oral Treatment | SGOT | Units/ml SGPT |
|---|---|---|
| Vehicle: | | |
| Water | 116 | 4 |
| Adraganth gum | 119 | 6 |
| CO-1 in water | 124 | 9 |
| CO-1 in adraganth gum | 132 | 10 |

TABLE 8

Subacute Toxicity of D in Female Rats

Daily Dose: 22 g/kg/day of D by gastric lavage for 21 days

| Oral Treatment | Dead/Treated | Body Weight in g (m ± SE) Start | Termination |
|---|---|---|---|
| Vehicle | 2/6(x) | 200.0 ± 4.1 | 233.2 5.1 |
| D, 2 g/kg/day | 1/6(x) | 204.1 ± 2.0 | 210.6 ± 9.6 |

(x) Death caused by a mistake in esophagus incannalutation. This diagnosis was confirmed at the post-mortem examination.

Daily Dose: 2 g/kg/day of D by gastric lavage for 21 days

| Oral Treatment | Average Percent Weight of Fresh Organs (m + SE) | | |
|---|---|---|---|
| | Lung | Liver | Kidneys |
| Vehicle (3 animals) | 0.85 ± 0.06 | 3.45 ± 0.07 | 0.95 ± 0.04 |
| D, (5 animals) | 1.07 ± 0.09NS | 4.54 ± 0.10NS(x) | 1.04 ± 0.03NS |

(x) Death caused by a mistake in esophagus incannalutation. This diagnosis was confirmed at the post mortem examination.

TABLE 9-continued

Chronic Toxicity in the Female Mouse
Daily treatment by gastric lavage for 18 weeks (4.5 months)

| | | | |
|---|---|---|---|
| D, 250 mg/kg/day | 0/10 | 27.3 ± 0.5 | 26.7 ± 0.7 | b. Urine excretion.
Urine amount excreted by 6 animals in 6 hours

| Oral Treatment | Urine Amount (ml) |
|---|---|
| Controls | 6 |
| D, 500 mg/kg/day | 7 |
| D, 250 mg/kg/day | 6.5 | c. Blood glucose. Mean values for 6 animals. Blood samples were taken 24 hours after the last dose

| Oral treatment | Blood Glucose |
|---|---|
| Controls | 1.14 |
| D, 500 mg/kg/day | 1.06 |
| D, 250 mg/kg/day | 1.10 | d. SGPT and SGOT. Mean values for 6 animals. Blood samples were taken 24 hours after the last dose

| Oral Treatment | Units/ml SGOT | SGPT |
|---|---|---|
| Controls | 125 | 5 |
| D, 500 mg/kg/day | 159 | 6 |
| D, 250 mg/kg/day | 118 | 5 |

Chronic Toxicity of D in the Female Mouse
e. Fresh Weights of Organs

| Oral Treatment | Fresh Organ-to-Body-Weight Ratio (m ± SE, 4 animals) | | | |
|---|---|---|---|---|
| | Kidneys | Heart | Liver | Lungs |
| Controls | 0.938 ± 0.044 | 0.481 ± 0.055 | 4.57 ± 0.15 | 0.674 ± 0.044 |
| D, 500 mg/kg/day | 1.07 ± 0.04 | 0.47 ± 0.02 | 4.66 ± 0.91 | 1.011 ± 0.110 |
| D, 250 mg/kg/day | 0.87 ± 0.08 | 0.60 ± 0.08 | 4.57 ± 0.25 | 0.731 ± 0.035 |

TABLE 10

Teratogenetic study a. Animal Species: Mouse, Male and female mice housed together for 10 days.
Oral treatment from 3rd day to 13th days.

| Oral treatment | Pregnant/Treated Animals | No. of living Foetuses per Delivery (m ± SE) | Body Weight of Foetuses in g (m ± SE) | No. of Foetuses with malformations |
|---|---|---|---|---|
| D, 250 mg/kg/day | 3/10(x) | 10.3 ± 0.6 | 1.42 ± 0.05 | 0 |
| Controls | 9/10 | 9.0 ± 0.9 | 1.46 ± 0.07 | 0 |

(x) On the basis of our wide experience, the above result might be casual. The study should be repeated to determine whether CO-1 actually prevents pregnancy.

b. Animal Species. Rat. Same experimental conditions as with the mouse.

| Oral Treatment | Pregnant/Treated Animals | No. of Living Foetuses per Delivery (m ± SE) | Body Weight of Foetuses in g (m ± SE) | No. of Foetuses with malformations |
|---|---|---|---|---|
| D, 250 mg/kg/day | 7/10 | 10.8 ± 0.86 | 7.08 ± 0.19 | 0 |
| Controls | 6/10 | 11.3 ± 1.12 | 6.82 ± 0.40 | 0 |

In view of the favourable sub-acute toxicity, the chronic toxicity in female mice was studied. The results are given in Table 9.

TABLE 9

Chronic Toxicity in the Female Mouse
Daily treatment by gastric lavage for 18 weeks (4.5 months)

a. Mortality and Body Weight

| Oral Treatment | Dead/Treated | Body Weight in g(m ± SE) Start | Termination |
|---|---|---|---|
| Vehicle | 3/10 | 28.2 ± 1 | 33.0 ± 1.1 |
| D, 500 mg/kg/day | 2/10 | 30.4 ± 0.9 | 30.0 ± 0.7 |

I claim:

1. A method for the treatment or prophylaxis of swine dysentery which comprises administering to swine an effective non-toxic amount of

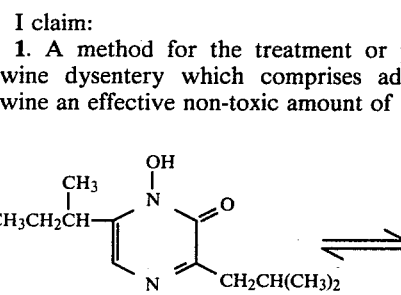

-continued

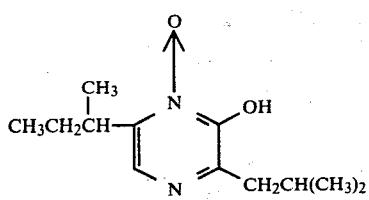

2. A swine feed composition having activity against swine dysentery-causing organisms comprising an edible swine feed carrier and dispersed therein, an effective non-toxic amount of

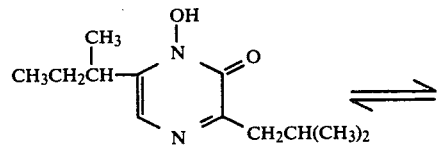

-continued

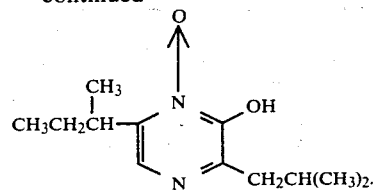

3. A feed composition according to claim 2 in which the pyrazine is present in an amount from about 25 g to about 500 g per ton of whole swine feed.

4. A comestible for ad libitum feeding to swine comprising a comestible swine feed carrier and dispersed therein, from about 100 to 200 g per ton of whole swine feed,

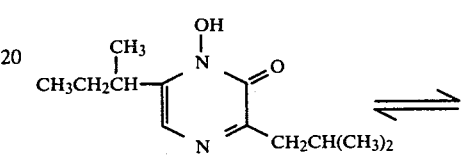

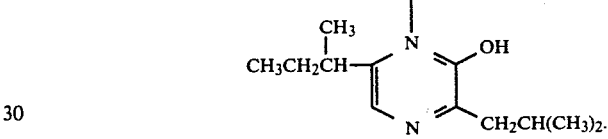

5. A comestible according to claim 4 in the form of a beverage.

* * * * *